United States Patent
Weisenburgh, II et al.

(10) Patent No.: US 10,945,779 B2
(45) Date of Patent: Mar. 16, 2021

(54) COMBINATION ULTRASONIC AND ELECTROSURGICAL INSTRUMENT HAVING ELECTRICALLY INSULATING FEATURES

(71) Applicant: ETHICON LLC, Guaynabo, PR (US)

(72) Inventors: William B. Weisenburgh, II, Maineville, OH (US); Jason R. Lesko, Cincinnati, OH (US); Catherine A. Corbett, Cincinnati, OH (US); Stephen M. Leuck, Milford, OH (US); Craig T. Davis, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 387 days.

(21) Appl. No.: 15/967,747

(22) Filed: May 1, 2018

(65) Prior Publication Data

US 2018/0333179 A1    Nov. 22, 2018

Related U.S. Application Data

(60) Provisional application No. 62/509,351, filed on May 22, 2017.

(51) Int. Cl.
*A61B 18/14* (2006.01)
*A61B 17/32* (2006.01)
(Continued)

(52) U.S. Cl.
CPC ...... *A61B 18/00* (2013.01); *A61B 17/320092* (2013.01); *A61B 18/1206* (2013.01);
(Continued)

(58) Field of Classification Search
CPC .... A61B 17/320068; A61B 17/320092; A61B 2017/00017; A61B 2017/00137;
(Continued)

(56) References Cited

U.S. PATENT DOCUMENTS 5,322,055 A    6/1994    Davison et al.
5,400,267 A    3/1995    Denen et al.
(Continued)

FOREIGN PATENT DOCUMENTS

DE    10 2014 116065 A1    5/2016
EP         2 371 314 A2    10/2011
(Continued)

OTHER PUBLICATIONS

U.S. Appl. No. 15/967,740, entitled "Combination Ultrasonic and Electrosurgical Instrument Having Electrical Circuits with Shared Return Path," filed May 1, 2018.

(Continued)

*Primary Examiner* — Michael F Peffley
*Assistant Examiner* — Khadijeh A Vahdat
(74) *Attorney, Agent, or Firm* — Frost Brown Todd LLC

(57) ABSTRACT

A surgical instrument includes a shaft, an ultrasonic transducer, a waveguide, and an end effector at a distal end of the shaft. The end effector includes an ultrasonic blade acoustically coupled with the waveguide, a clamp arm movable relative to the ultrasonic blade, a first RF electrode provided by the clamp arm, and a second RF electrode provided by the ultrasonic blade. The first RF electrode is electrically coupled with a first RF electrical path of the instrument, and the second RF electrode is electrically coupled with a second RF electrical path of the instrument. The RF electrodes are operable to seal tissue with bipolar RF energy. An electrically insulative layer is provided on at least a portion of at least one of the ultrasonic blade, the waveguide, the shaft, or the clamp arm, and is configured to prevent shorting between the first and second RF electrical paths.

20 Claims, 13 Drawing Sheets

(51) Int. Cl.
*A61B 18/00* (2006.01)
*A61B 18/12* (2006.01)
A61B 17/00 (2006.01)
A61B 17/29 (2006.01)
A61B 90/00 (2016.01)

(52) U.S. Cl.
CPC ............ *A61B 18/1445* (2013.01); *A61B 2017/00017* (2013.01); *A61B 2017/00137* (2013.01); *A61B 2017/2929* (2013.01); *A61B 2017/2932* (2013.01); *A61B 2017/320072* (2013.01); *A61B 2017/320074* (2017.08); *A61B 2017/320075* (2017.08); *A61B 2017/320078* (2017.08); *A61B 2017/320088* (2013.01); *A61B 2017/320094* (2017.08); *A61B 2017/320095* (2017.08); *A61B 2018/0063* (2013.01); *A61B 2018/00077* (2013.01); *A61B 2018/00083* (2013.01); *A61B 2018/00607* (2013.01); *A61B 2018/00988* (2013.01); *A61B 2018/00994* (2013.01); *A61B 2018/126* (2013.01); *A61B 2018/1452* (2013.01); *A61B 2018/1457* (2013.01); *A61B 2090/0803* (2016.02)

(58) Field of Classification Search
CPC ........... A61B 2017/00738; A61B 2017/00929; A61B 2017/2929; A61B 2017/2932; A61B 2017/320072; A61B 2017/320074; A61B 2017/320075; A61B 2017/320078; A61B 2017/320088; A61B 2017/320094; A61B 2017/320095; A61B 18/00; A61B 18/12; A61B 18/1206; A61B 18/14; A61B 18/1445; A61B 2018/00077; A61B 2018/00083; A61B 2018/00136; A61B 2018/00178; A61B 2018/00577; A61B 2018/00607; A61B 2018/0063; A61B 2018/00988; A61B 2018/00994; A61B 2018/126; A61B 2018/142; A61B 2018/1452; A61B 2018/1457; A61B 2018/0803
See application file for complete search history.

(56) References Cited

U.S. PATENT DOCUMENTS

| | | | |
|---|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,231,565 B1 | 5/2001 | Tovey et al. |
| 6,283,981 B1 | 9/2001 | Beaupre |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,025,630 B2 | 9/2011 | Murakami et al. |
| 8,057,498 B2 | 11/2011 | Robertson |
| 8,147,488 B2 | 4/2012 | Masuda |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,939,974 B2 | 1/2015 | Boudreaux et al. |
| 8,986,302 B2 | 3/2015 | Aldridge et al. |
| 9,017,326 B2 | 4/2015 | DiNardo et al. |
| 9,039,690 B2 | 5/2015 | Kersten et al. |
| 9,089,327 B2 | 7/2015 | Worrell et al. |
| 9,095,367 B2 | 8/2015 | Olson et al. |
| 9,101,385 B2 | 8/2015 | Shelton, IV et al. |
| 9,107,690 B2 | 8/2015 | Bales, Jr. et al. |
| 9,161,803 B2 | 10/2015 | Yates et al. |
| 9,301,759 B2 | 4/2016 | Spivey et al. |
| 9,402,682 B2 | 8/2016 | Worrell et al. |
| 9,545,253 B2 | 1/2017 | Worrell et al. |
| 9,572,622 B2 | 2/2017 | Shelton, IV et al. |
| 9,681,912 B2 | 6/2017 | Tsubuku et al. |
| 9,901,754 B2 | 2/2018 | Yamada |
| 9,962,222 B2 | 5/2018 | Brustad et al. |
| 10,010,340 B2 | 7/2018 | Hibner et al. |
| 10,028,765 B2 | 7/2018 | Hibner et al. |
| 10,039,595 B2 | 8/2018 | Sakaguchi et al. |
| 10,201,364 B2 | 2/2019 | Leimbach et al. |
| 2012/0078243 A1 | 3/2012 | Worrell et al. |
| 2014/0135804 A1 | 5/2014 | Weisenburgh, II et al. |
| 2014/0163541 A1 | 6/2014 | Shelton, IV et al. |
| 2014/0239037 A1 | 8/2014 | Boudreaux et al. |
| 2015/0088178 A1 | 3/2015 | Stulen et al. |
| 2015/0141981 A1 | 5/2015 | Price et al. |
| 2015/0164538 A1* | 6/2015 | Aldridge .............. F15D 1/0015 606/52 |
| 2015/0358426 A1 | 12/2015 | Kimball et al. |
| 2015/0374360 A1 | 12/2015 | Scheib et al. |
| 2016/0022305 A1 | 1/2016 | Lamping et al. |
| 2016/0302820 A1 | 10/2016 | Hibner et al. |
| 2016/0324537 A1 | 11/2016 | Green et al. |
| 2016/0367281 A1 | 12/2016 | Gee et al. |
| 2017/0000515 A1 | 1/2017 | Akagane |
| 2017/0000516 A1 | 1/2017 | Stulen et al. |
| 2017/0000541 A1 | 1/2017 | Yates et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0105754 A1 | 4/2017 | Boudreaux et al. |
| 2018/0116688 A1 | 5/2018 | Akagane |
| 2018/0333182 A1 | 11/2018 | Clauda |

FOREIGN PATENT DOCUMENTS

| | | |
|---|---|---|
| EP | 2 478 861 A2 | 7/2012 |
| EP | 2 641 552 A2 | 9/2013 |
| EP | 3 031 417 A1 | 6/2016 |
| EP | 3 117 790 A1 | 1/2017 |
| EP | 3 287 085 A1 | 2/2018 |
| WO | WO 2016/091400 A1 | 6/2016 |
| WO | WO 2017/027853 A1 | 2/2017 |
| WO | WO 2017/058617 A2 | 4/2017 |
| WO | WO 2017/091377 A1 | 6/2017 |
| WO | WO 2017/100427 A2 | 6/2017 |

(56) References Cited

OTHER PUBLICATIONS

U.S. Appl. No. 15/967,746, entitled "Combination Ultrasonic and Electrosurgical Instrument Having Slip Ring Electrical Contact Assembly," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with Adjustable Energy Modalities and Method for Sealing Tissue and Inhibiting Tissue Resection," filed May 1, 2018.
U.S. Appl. No. 15/967,764, entitled "Combination Ultrasonic and Electrosurgical System Having EEPROM and ASIC Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.
U.S. Appl. No. 15/967,740.
U.S. Appl. No. 15/967,746.
U.S. Appl. No. 15/967,751.
U.S. Appl. No. 15/967,753.
U.S. Appl. No. 15/967,759.
U.S. Appl. No. 15/967,761; and.
U.S. Appl. No. 15/967,764.
International Search Report and Written Opinion dated Aug. 22, 2018 for Application No. PCT/US2018/033599, 14 pgs.
International Search Report and Written Opinion dated Jan. 2, 2019 for Application No. PCT/US2018/033603, 23 pgs.
International Search Report and Written Opinion dated Nov. 6, 2018 for Application No. PCT/US2018/033605, 14 pgs.
International Search Report and Written Opinion dated Jan. 2, 2019 for Application No. PCT/US2018/033607, 22 pgs.
International Search Report and Written Opinion dated Nov. 6, 2018 for Application No. PCT/US2018/033608, 14 pgs.
International Search Report and Written Opinion dated Sep. 3, 2018 for Application No. PCT/US2018/033615, 13 pgs.
International Search Report and Written Opinion dated Aug. 22, 2018 for Application No. PCT/US2018/033618, 12 pgs.
International Search Report and Written Opinion dated Oct. 19, 2018 for Application No. PCT/US2018/033619, 20 pgs.
U.S. Appl. No. 62/509,351, entitled "Ultrasonic Instrument With Electrosurgical Features," filed May 22, 2017.

\* cited by examiner

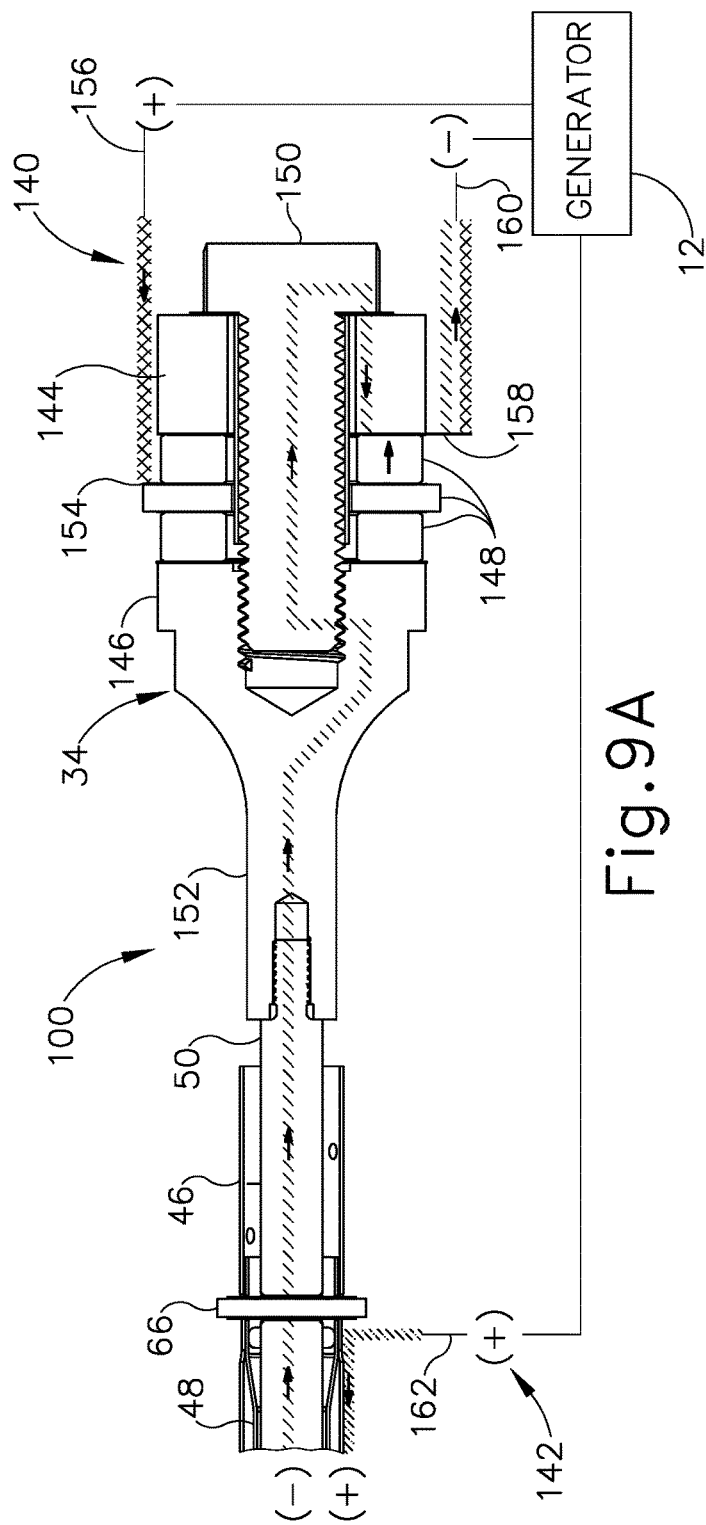
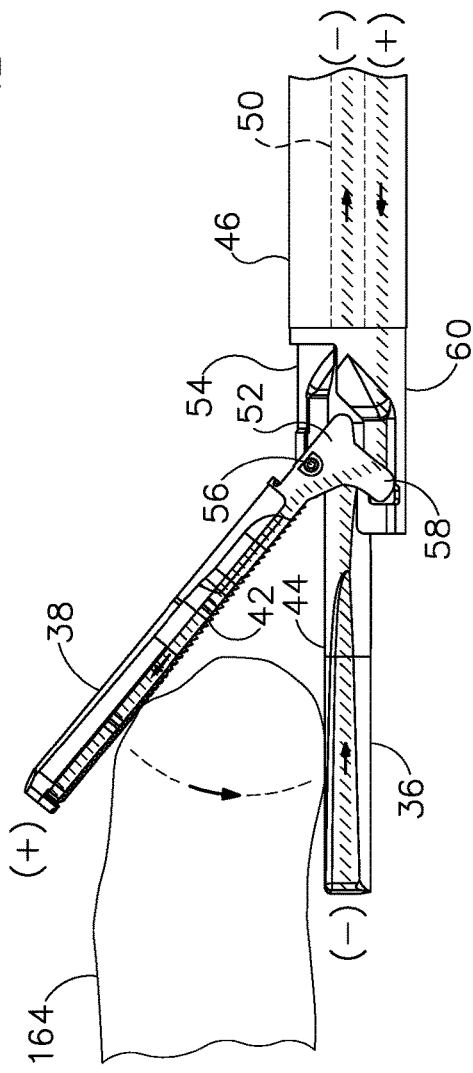

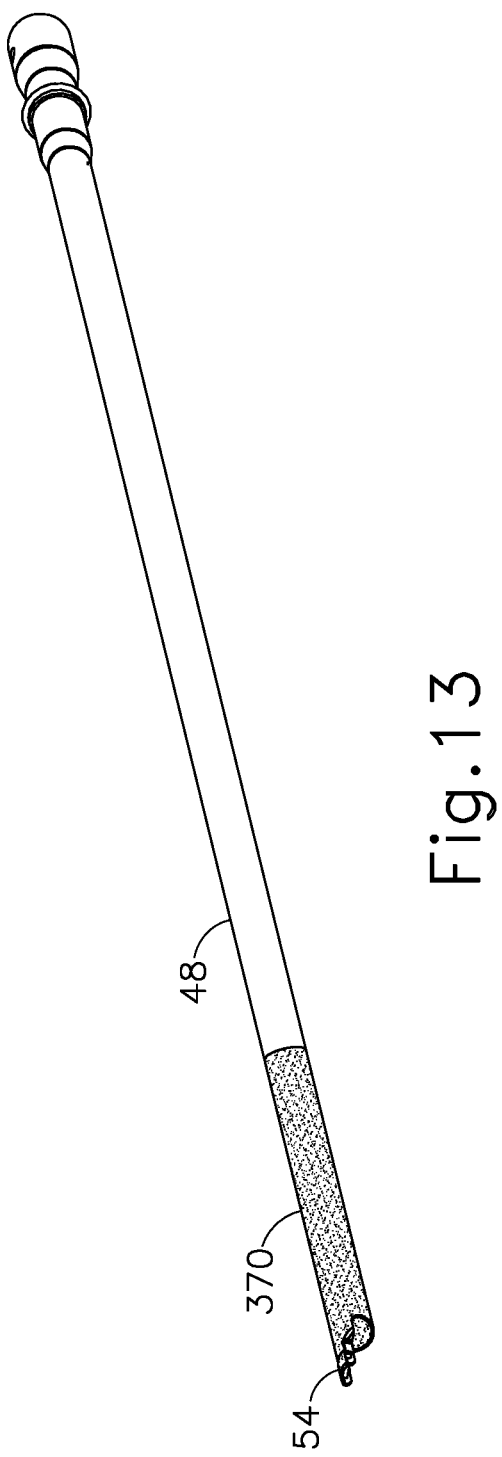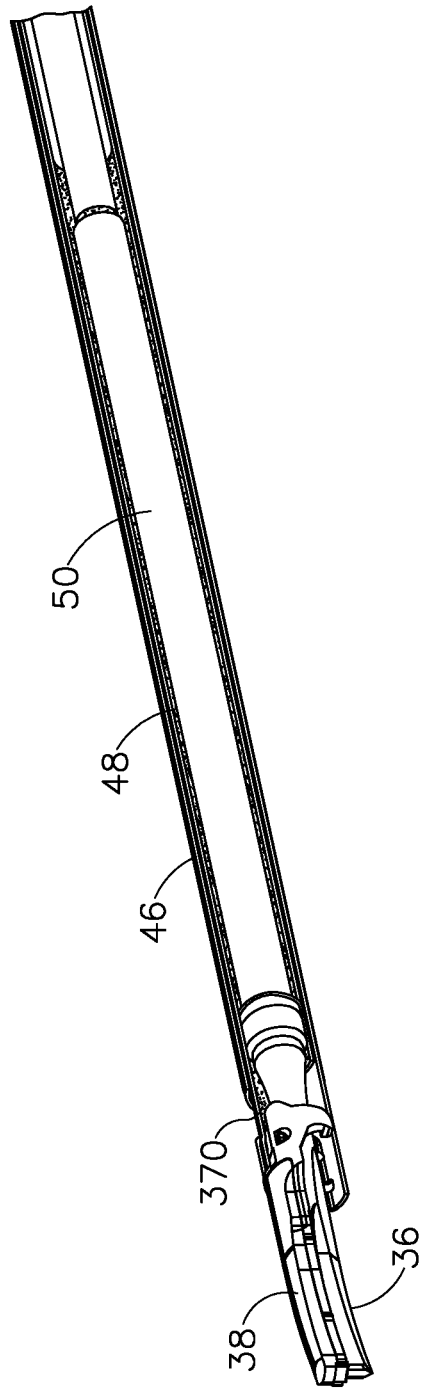

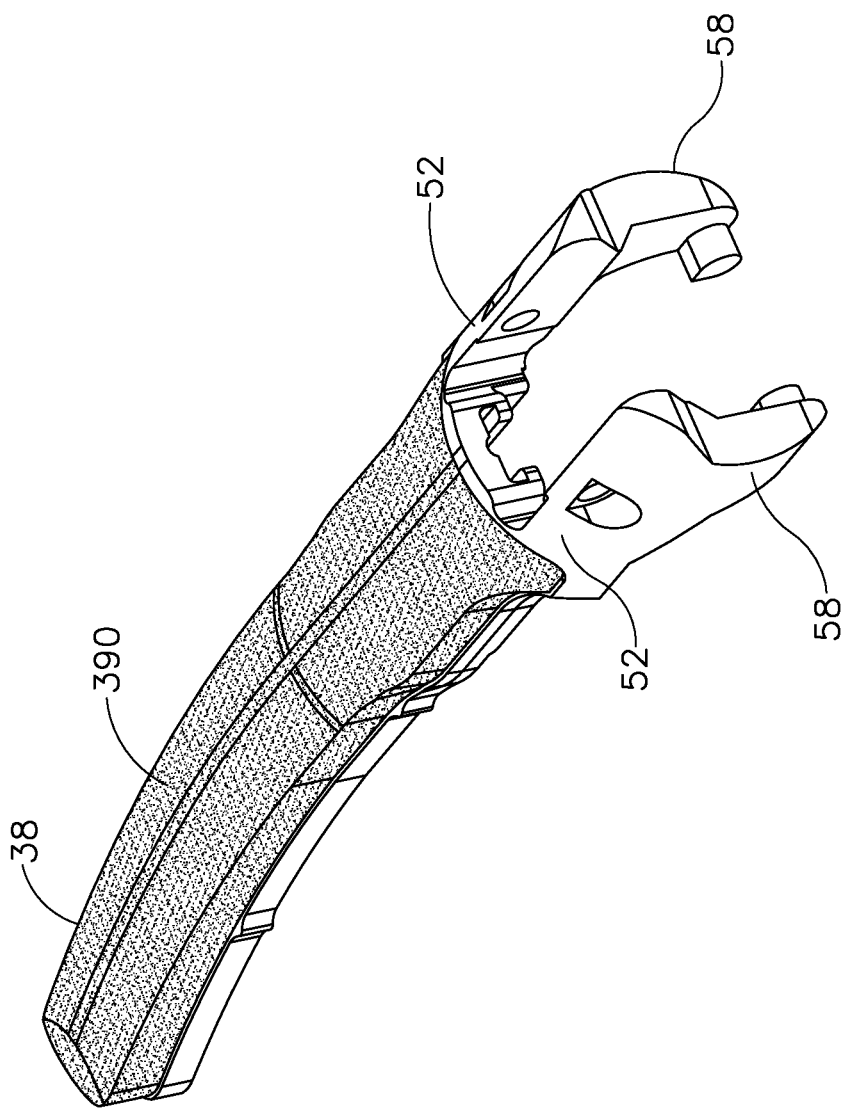

2013 YOUNES US 10,945,779 B2

COMBINATION ULTRASONIC AND ELECTROSURGICAL INSTRUMENT HAVING ELECTRICALLY INSULATING FEATURES

This application claims the benefit of U.S. Provisional App. No. 62/509,351, entitled "Ultrasonic Instrument With Electrosurgical Features," filed May 22, 2017, the disclosure of which is incorporated by reference herein.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 13 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, OH. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit lower frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

While various types of ultrasonic surgical instruments and electrosurgical instruments, including combination ultrasonic-electrosurgical instruments, have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9A depicts a schematic view of portions of the surgical system of FIG. 1, showing active and return paths of an ultrasonic electrical circuit and a bipolar RF electrical circuit passing through the surgical instrument;

FIG. 9B depicts a schematic view of the end effector of the surgical instrument of FIG. 9A, showing the active path of the RF electrical circuit passing distally from the outer tube to the clamp arm into tissue, and the return path passing proximally from the tissue to the ultrasonic blade and into the waveguide;

FIG. 13 depicts a perspective view of the inner tube of the ultrasonic instrument of FIG. 1, having an electrically insulative material applied to outer and inner surfaces thereof;

FIG. 14 depicts a sectional perspective view of the end effector and shaft assembly of the surgical instrument of FIG. 1, incorporating the treated inner tube of FIG. 13;

FIG. 17 depicts a perspective view of the clamp arm of the surgical instrument of FIG. 1, having an electrically insulative material applied to a non-clamping outer side thereof.

Figure 1:
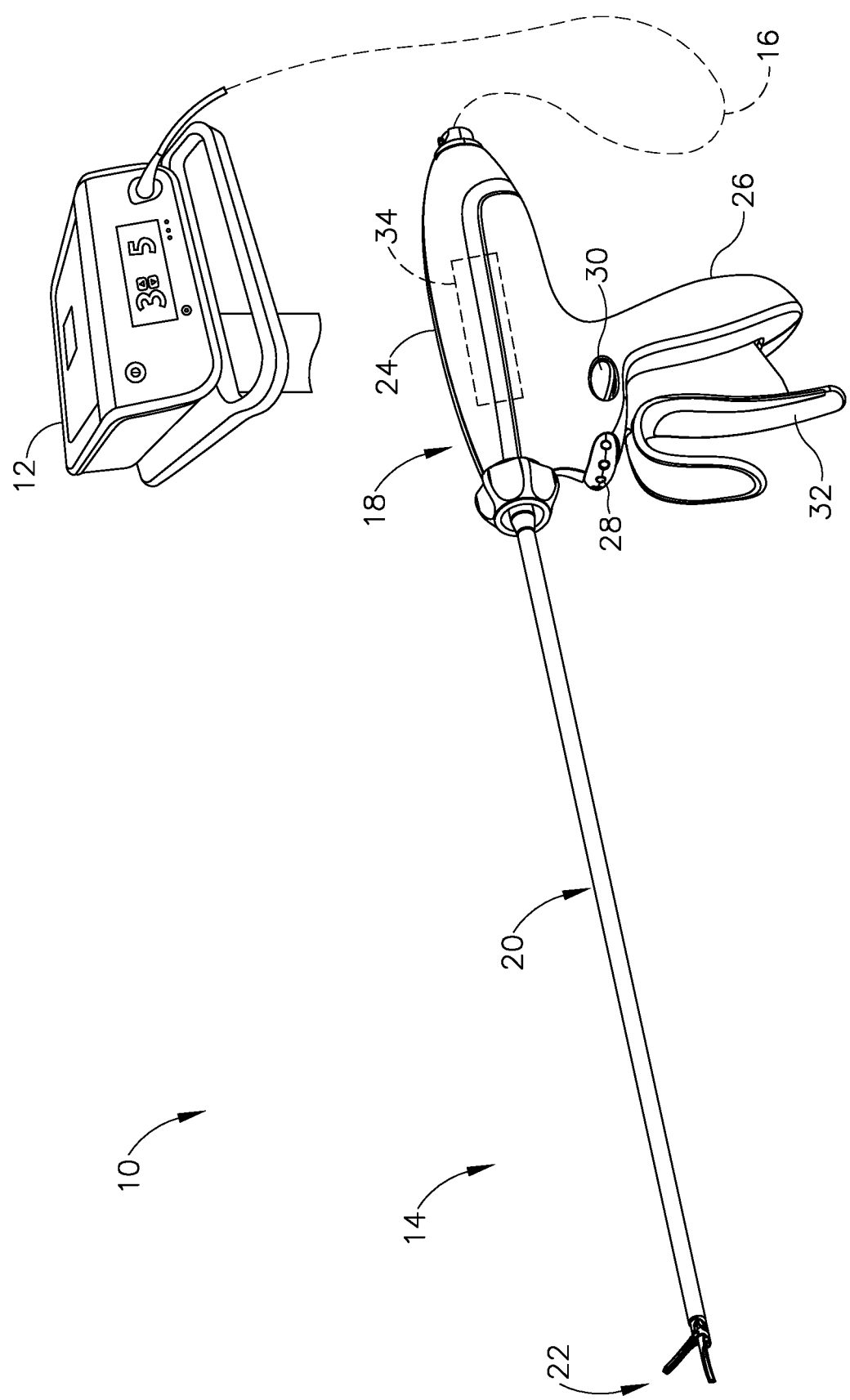
FIG. 1 depicts a perspective view of an exemplary surgical system having a generator and a surgical instrument operable to treat tissue with ultrasonic energy and bipolar RF energy.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical System

FIG. 1 depicts an exemplary surgical system (10) including a generator (12) and a surgical instrument (14). Surgical instrument (14) is operatively coupled with the generator (12) via power cable (16). As described in greater detail below, generator (12) is operable to power surgical instrument (14) to deliver ultrasonic energy for cutting tissue, and electrosurgical bipolar RF energy (i.e., therapeutic levels of RF energy) for sealing tissue. In exemplary configurations, generator (12) is configured to power surgical instrument (14) to deliver ultrasonic energy and electrosurgical bipolar RF energy simultaneously.

A. Overview of Exemplary Surgical Instrument with Ultrasonic and Electrosurgical Features Surgical instrument (14) of the present example comprises a handle assembly (18), a shaft assembly (20) extending distally from the handle assembly (18), and an end effector (22) arranged at a distal end of the shaft assembly (20). Handle assembly (18) comprises a body (24) including a pistol grip (26) and energy control buttons (28, 30) configured to be manipulated by a surgeon. A trigger (32) is coupled to a lower portion of body (24) and is pivotable toward and away from pistol grip (26) to selectively actuate end effector (22), as described in greater detail below. In other suitable variations of surgical instrument (14), handle assembly (18) may comprise a scissor grip configuration, for example. As described in greater detail below, an ultrasonic transducer (34) is housed internally within and supported by body (24). In other configurations, ultrasonic transducer (34) may be provided externally of body (24).

Figure 2:
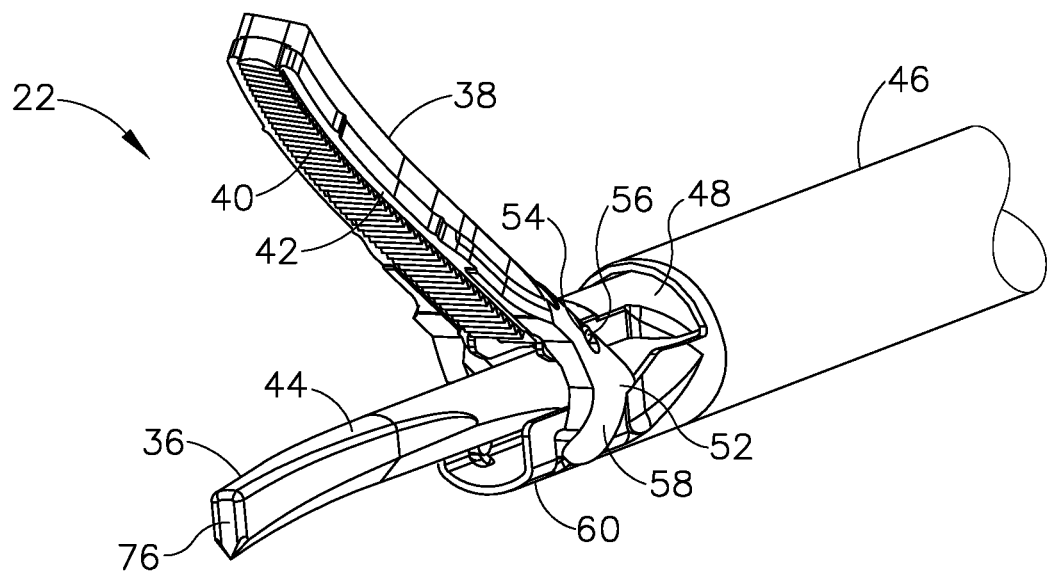
FIG. 2 depicts a top perspective view of an end effector of the surgical instrument of FIG. 1, having a clamp arm that provides a first electrode and an ultrasonic blade that provides a second electrode.
Figure 3:
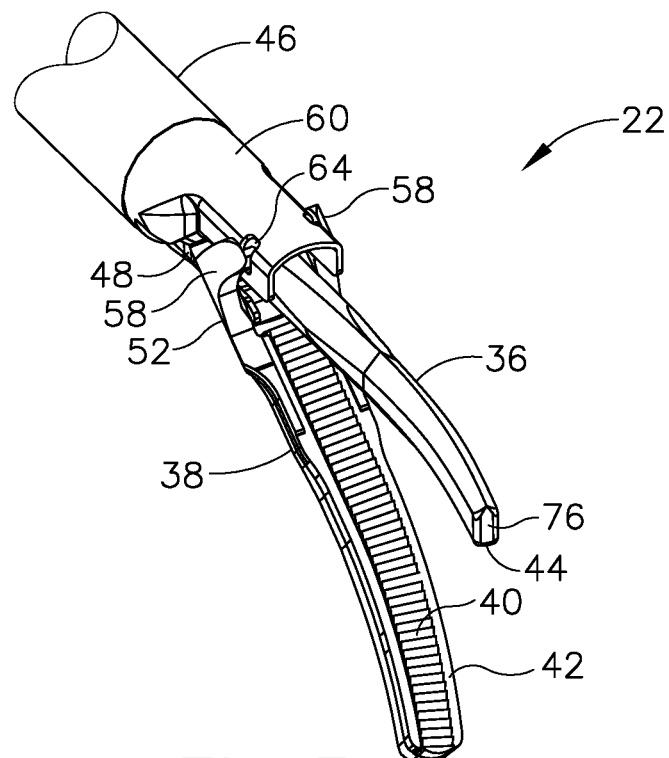
FIG. 3 depicts a bottom perspective view of the end effector of FIG. 2.

As shown in FIGS. 2 and 3, end effector (22) includes an ultrasonic blade (36) and a clamp arm (38) configured to selectively pivot toward and away from ultrasonic blade (36), for clamping tissue therebetween. Ultrasonic blade (36) is acoustically coupled with ultrasonic transducer (34), which is configured to drive (i.e., vibrate) ultrasonic blade (36) at ultrasonic frequencies for cutting and/or sealing tissue positioned in contact with ultrasonic blade (36). Clamp arm (38) is operatively coupled with trigger (32) such that clamp arm (38) is configured to pivot toward ultrasonic blade (36), to a closed position (see e.g., FIG. 16), in response to pivoting of trigger (32) toward pistol grip (26). Further, clamp arm (38) is configured to pivot away from ultrasonic blade (36), to an open position (see e.g., FIGS. 1-3), in response to pivoting of trigger (32) away from pistol grip (26). Various suitable ways in which clamp arm (38) may be coupled with trigger (32) will be apparent to those of ordinary skill in the art in view of the teachings provided herein. In some versions, one or more resilient members may be incorporated to bias clamp arm (38) and/or trigger (32) toward the open position.

A clamp pad (40) is secured to and extends distally along a clamping side of clamp arm (38), facing ultrasonic blade (36). Clamp pad (40) is configured to engage and clamp tissue against a corresponding tissue treatment portion of ultrasonic blade (36) when clamp arm (38) is actuated to its closed position. At least a clamping-side of clamp arm (38) provides a first electrode (42), referred to herein as clamp arm electrode (42). Additionally, at least a clamping-side of ultrasonic blade (36) provides a second electrode (44), referred to herein as a blade electrode (44). As described in greater detail below, electrodes (42, 44) are configured to apply electrosurgical bipolar RF energy, provided by generator (12), to tissue electrically coupled with electrodes (42, 44). Clamp arm electrode (42) may serve as an active electrode while blade electrode (44) serves as a return electrode, or vice-versa. Surgical instrument (14) may be configured to apply the electrosurgical bipolar RF energy through electrodes (42, 44) while vibrating ultrasonic blade (36) at an ultrasonic frequency, before vibrating ultrasonic blade (36) at an ultrasonic frequency, and/or after vibrating ultrasonic blade (36) at an ultrasonic frequency.

As shown in FIGS. 1-5, shaft assembly (20) extends along a longitudinal axis and includes an outer tube (46), an inner tube (48) received within outer tube (46), and an ultrasonic waveguide (50) supported within inner tube (48). As seen best in FIGS. 2-5, clamp arm (38) is coupled to distal ends of inner and outer tubes (46, 48). In particular, clamp arm (38) includes a pair of proximally extending clevis arms (52) that receive therebetween and pivotably couple to a distal end (54) of inner tube (48) with a pivot pin (56) received within through bores formed in clevis arms (52) and distal end (54) of inner tube (48). First and second clevis fingers (58) depend downwardly from clevis arms (52) and pivotably couple to a distal end (60) of outer tube (46). Specifically, each clevis finger (58) includes a protrusion (62) that is rotatably received within a corresponding opening (64) formed in a sidewall of distal end (60) of outer tube (46).

In the present example, inner tube (48) is longitudinally fixed relative to handle assembly (18), and outer tube (46) is configured to translate relative to inner tube (48) and handle assembly (18), along the longitudinal axis of shaft assembly (20). As outer tube (46) translates distally, clamp arm (38) pivots about pivot pin (56) toward its open position. As outer tube (46) translates proximally, clamp arm (38) pivots in an opposite direction toward its closed position. As described below with reference to FIG. 11, a proximal end of outer tube (46) is operatively coupled with trigger (32), for example via a linkage assembly, such that actuation of trigger (32) causes translation of outer tube (46) relative to inner tube (48), thereby opening or closing clamp arm (38). In other suitable configurations not shown herein, outer tube (46) may be longitudinally fixed and inner tube (48) may be configured to translate for moving clamp arm (38) between its open and closed positions.

Shaft assembly (20) and end effector (22) are configured to rotate together about the longitudinal axis, relative to handle assembly (18). A retaining pin (66), shown in FIG. 4, extends transversely through proximal portions of outer tube (46), inner tube (48), and waveguide (50) to thereby couple these components rotationally relative to one another. In the present example, a rotation knob (68) is provided at a proximal end portion of shaft assembly (20) to facilitate rotation of shaft assembly (20), and end effector (22), relative to handle assembly (18). Rotation knob (68) is secured rotationally to shaft assembly (20) with retaining pin (66), which extends through a proximal collar of rotation knob (68). It will be appreciated that in other suitable configurations, rotation knob (68) may be omitted or substituted with alternative rotational actuation structures.

Figure 5:
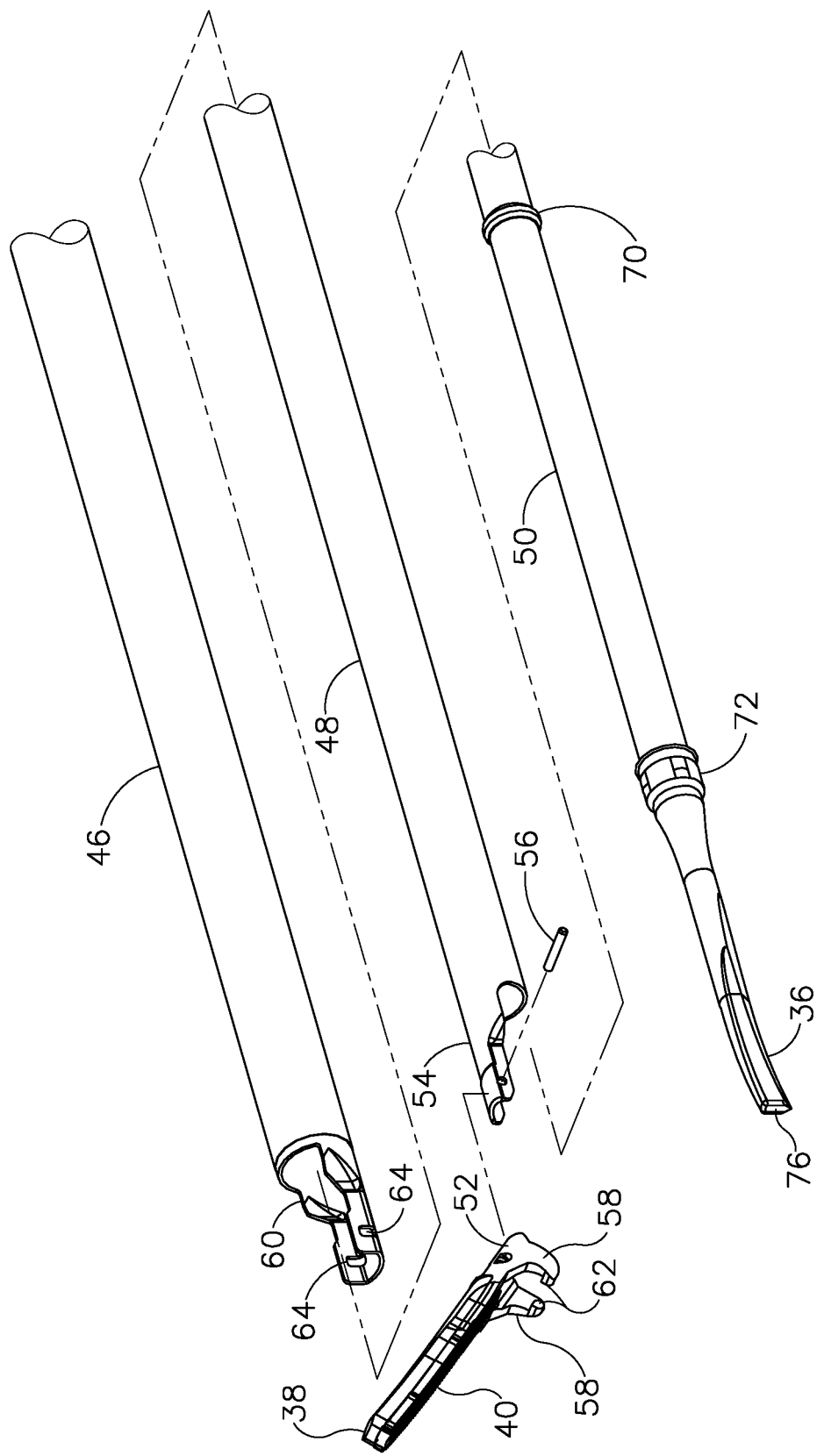
FIG. 5 depicts an enlarged exploded perspective view of a distal portion of the shaft assembly and the end effector of the surgical instrument of FIG. 1.

Ultrasonic waveguide (50) is acoustically coupled at its proximal end with ultrasonic transducer (34), for example by a threaded connection, and at its distal end with ultrasonic blade (36), as shown in FIG. 5. Ultrasonic blade (36) is shown formed integrally with waveguide (50) such that blade (36) extends distally, directly from the distal end of waveguide (50). In this manner, waveguide (50) acoustically couples ultrasonic transducer (34) with ultrasonic blade (36), and functions to communicate ultrasonic mechanical vibrations from transducer (34) to blade (36). Accordingly, ultrasonic transducer (34), waveguide (50), and ultrasonic blade (36) together define acoustic assembly (100). During use, ultrasonic blade (36) may be positioned in direct contact with tissue, with or without assistive clamping force provided by clamp arm (38), to impart ultrasonic vibrational energy to the tissue and thereby cut and/or seal the tissue. For example, blade (36) may cut through tissue clamped between clamp arm (38) and a first treatment side of blade (36), or blade (36) may cut through tissue positioned in contact with an oppositely disposed second treatment side of blade (36), for example during a "back-cutting" movement. In some variations, waveguide (50) may amplify the ultrasonic vibrations delivered to blade (36). Further, waveguide (50) may include various features operable to control the gain of the vibrations, and/or features suitable to tune waveguide (50) to a selected resonant frequency. Additional exemplary features of ultrasonic blade (36) and waveguide (50) are described in greater detail below.

Figure 4:
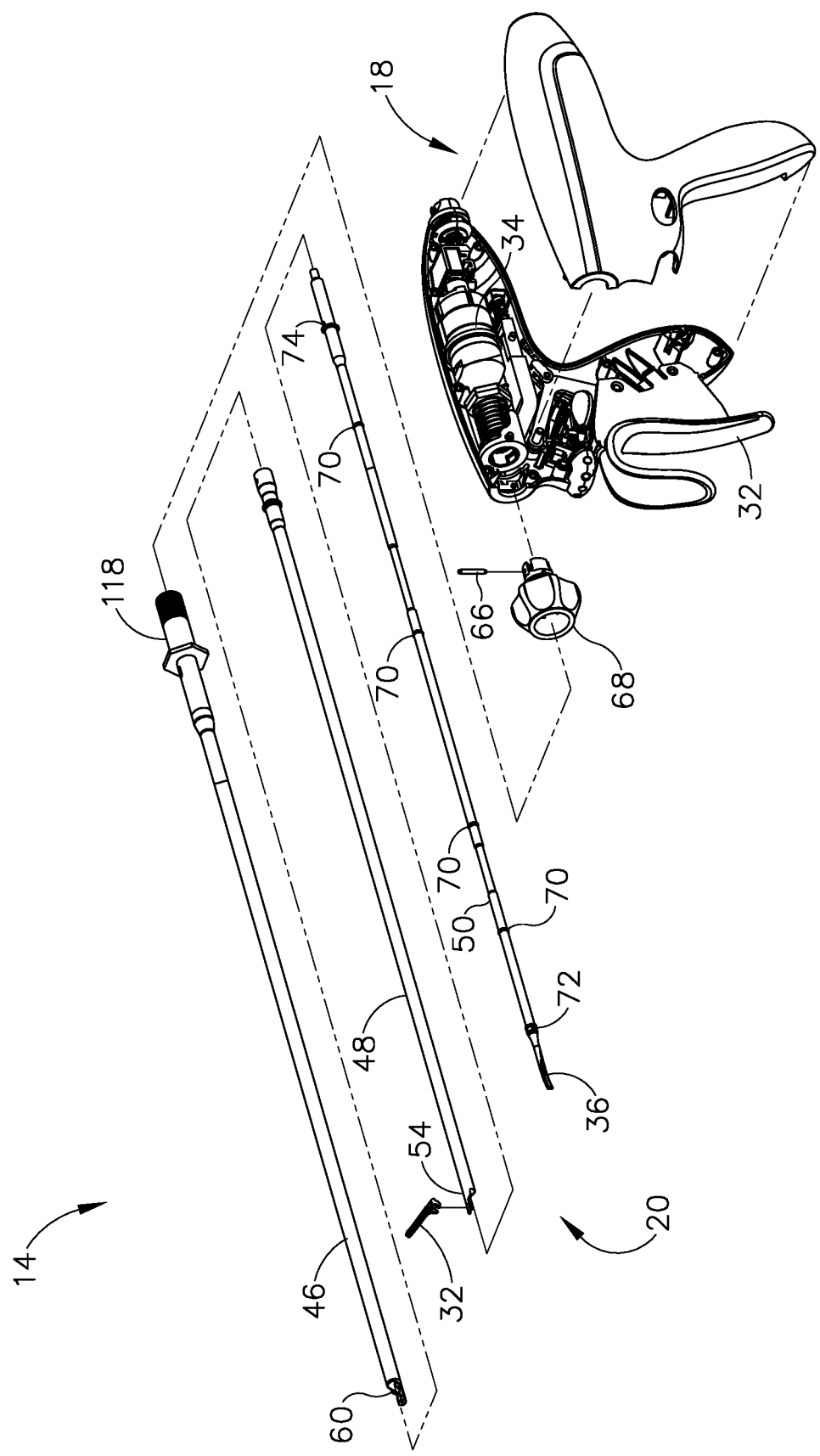
FIG. 4 depicts a partially exploded perspective view of the surgical instrument of FIG. 1.

Waveguide (50) is supported within inner tube (48) by a plurality of nodal support elements (70) positioned along a length of waveguide (50), as shown in FIGS. 4 and 5. Specifically, nodal support elements (70) are positioned longitudinally along waveguide (50) at locations corresponding to acoustic nodes defined by the resonant ultrasonic vibrations communicated through waveguide (50). Nodal support elements (70) may provide structural support to waveguide (50), and acoustic isolation between waveguide (50) and inner and outer tubes (46, 48) of shaft assembly (20). In exemplary variations, nodal support elements (70) may comprise o-rings. Waveguide (50) is supported at its distal-most acoustic node by a nodal support element in the form of an overmold member (72), shown in FIG. 5 and described in greater detail below with reference to FIG. 43. Waveguide (50) is secured longitudinally and rotationally within shaft assembly (20) by retaining pin (66), which passes through a transverse through-bore (74) formed at a proximally arranged acoustic node of waveguide (50), such as the proximal-most acoustic node, for example.

In the present example, a distal tip (76) of ultrasonic blade (36) is located at a position corresponding to an anti-node associated with the resonant ultrasonic vibrations communicated through waveguide (50). Such a configuration enables the acoustic assembly (100) of instrument (14) to be tuned to a preferred resonant frequency $f_o$ when ultrasonic blade (36) is not loaded by tissue. When ultrasonic transducer (34) is energized by generator (12) to transmit mechanical vibrations through waveguide (50) to blade (36), distal tip (76) of blade (36) is caused to oscillate longitudinally in the range of approximately 20 to 120 microns peak-to-peak, for example, and in some instances in the range of approximately 20 to 50 microns, at a predetermined vibratory frequency $f_o$ of approximately 50 kHz, for example. When ultrasonic blade (36) is positioned in contact with tissue, the ultrasonic oscillation of blade (36) may simultaneously sever the tissue and denature the proteins in adjacent tissue cells, thereby providing a coagulative effect with minimal thermal spread.

Figure 6:
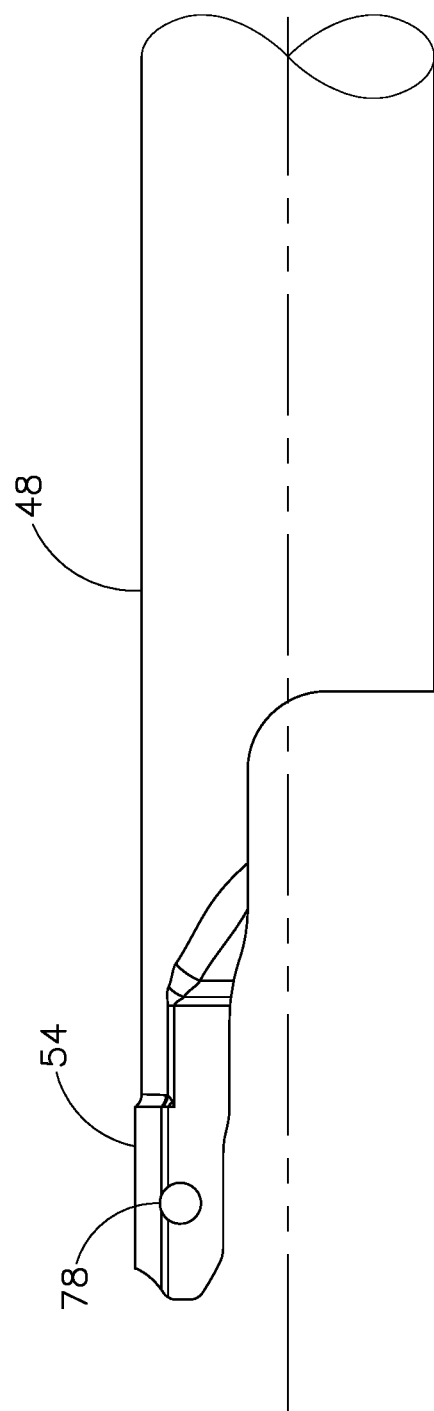
FIG. 6 depicts a side elevational view of a distal portion of an inner tube of the shaft assembly of the surgical instrument of FIG. 1.

As shown in FIG. 6, distal end (54) of inner tube (48) may be offset radially outwardly relative to a remaining proximal portion of inner tube (48). This configuration enables pivot pin bore (78), which receives clamp arm pivot pin (56), to be spaced further away from the longitudinal axis of shaft assembly (20) than if distal end (54) where formed flush with the remaining proximal portion of inner tube (48). Advantageously, this provides increased clearance between proximal portions of clamp arm electrode (42) and blade electrode (44), thereby mitigating risk of undesired "shorting" between electrodes (42, 44) and their corresponding active and return electrical paths, for example during back-cutting when ultrasonic blade (36) flexes toward clamp arm (38) and pivot pin (56) in response to normal force exerted on blade (36) by tissue. In other words, when ultrasonic blade (36) is used in a back-cutting operation, ultrasonic blade (36) may tend to deflect slightly away from the longitudinal axis of shaft assembly (20), toward pin (56). By having pivot pin bore (78) spaced further away from the longitudinal axis than pivot pin bore (78) otherwise would be in the absence of the radial offset provided by distal end (54) of the present example, distal end (54) provides additional lateral clearance between pivot pin (56) and ultrasonic blade (36), thereby reducing or eliminating the risk of contact between ultrasonic blade (36) and pivot pin (56) when ultrasonic blade (36) deflects laterally during back-cutting operations. In addition to preventing electrical short circuits that would otherwise result from contact between ultrasonic blade (36) and pivot pin (56) when end effector (22) is activated to apply RF electrosurgical energy, the additional clearance prevents mechanical damage that might otherwise result from contact between ultrasonic blade (36) and pivot pin (56) when ultrasonic blade (36) is vibrating ultrasonically.

B. Exemplary Handle and Shaft Assemblies

Figure 7:
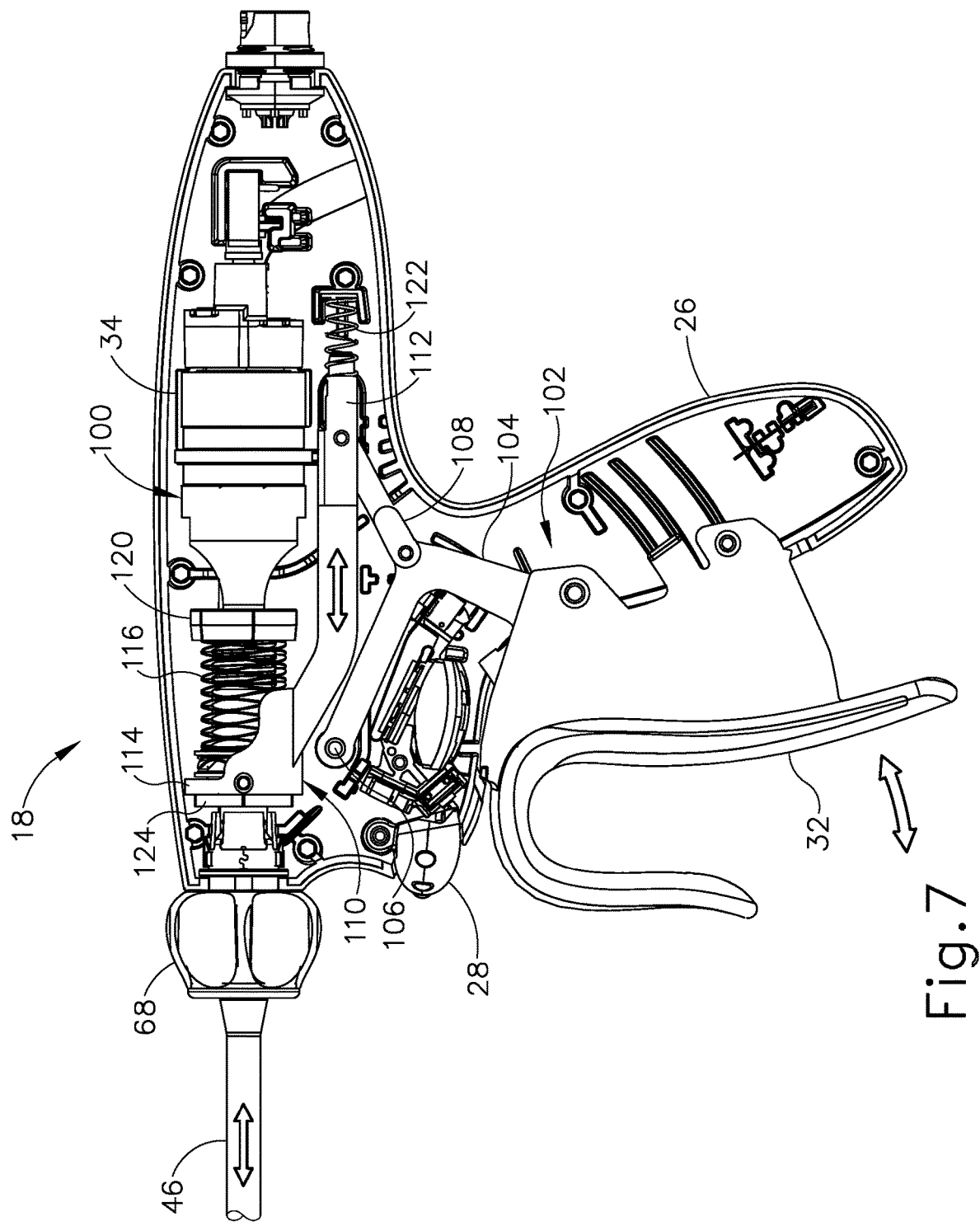
FIG. 7 depicts a side elevational view of a handle assembly of the surgical instrument of FIG. 1, with a side portion of the body of the handle assembly omitted to expose internal components, including an actuation assembly having a trigger and an acoustic assembly having an ultrasonic transducer.

FIG. 7 shows additional details of features housed within handle assembly (18) of surgical instrument (14), including an acoustic assembly (100) and an actuation assembly (102). Acoustic assembly (100) is described in greater detail below with reference to FIG. 9A. Actuation assembly (102) includes trigger (32) and a series of links that operatively couple trigger (32) with outer tube (46) and thus clamp arm (38), such that pivoting of trigger (32) relative to body (24) may cause pivoting of clamp arm (38) relative to ultrasonic blade (36). More specifically, trigger (32) is coupled to a first link (104) that pivots about pivot point (106). First link (104) is pivotably coupled at a medial elbow portion thereof to a distal end of a second link (108). Second link (108) is pivotably at its proximal end to a proximal arm (112) of a translating member (110). Arm (112) is rigidly connected at its distal end to a yoke (114) of translating member (110). Yoke (114) at least partially encircles and operatively couples with a proximal end of outer tube (46). In particular, yoke (114) abuts a distal end of a spring stack (116) that is retained on a cylindrical spring retainer (118) (see FIG. 8) by a proximal retaining nut (120). Spring stack (116) comprises a linearly arranged array of adjacent wave springs in this example. Spring retainer (118) fixedly couples to a proximal end of outer tube (46).

As indicated by directional arrows in FIG. 7, squeezing trigger (32) toward pistol grip (26) actuates outer tube (46) proximally to thereby close clamp arm (38), and releasing trigger (32) enables outer tube to actuate distally to thereby open clamp arm (38). In particular, moving trigger (32) toward pistol grip (26) (e.g., by squeezing) causes first and second links (104, 108) to pivot about their respective pivot axes and drive translating member (110) proximally along the longitudinal axis of shaft assembly (20). Proximal movement of translating member (110) causes yoke (114) to compress spring stack (116) proximally against retaining nut (120), which drives spring retainer (118) and outer tube (46) proximally. As described above, proximal translation of outer tube (46) causes clamp arm (38) to pivot toward its closed position.

In the present example, actuation assembly (102) further includes a compression spring (122) arranged at a proximal end of arm (112) of translating member (110), and which biases translating member (110) distally. When trigger (32) is released, compression spring (122) drives translating member distally so that yoke (114) engages a distal flange (124) of spring retainer (118). Because spring retainer (118) is fixed to outer tube (46), yoke (114) drives spring retainer and outer tube (46) distally together, which causes clamp arm (38) to return to its open position.

Though not shown herein, it will be appreciated that actuation assembly (102) may be supplemented or substituted with a motor assembly configured to provide powered actuation of clamp arm (38). Exemplary surgical devices incorporating motor assemblies are disclosed in U.S. Pat. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. Pub. No. 2015/0374360, entitled "Articulation Drive Features for Surgical Stapler," published Dec. 31, 2015, issued as U.S. Pat. No. 10,292,701 on May 21, 2019, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, incorporated by reference above; and U.S. Pat. No. 9,161,803, entitled "Motor Driven Electrosurgical Device with Mechanical and Electrical Feedback," issued Oct. 20, 2015, incorporated by reference above.

Figure 8:
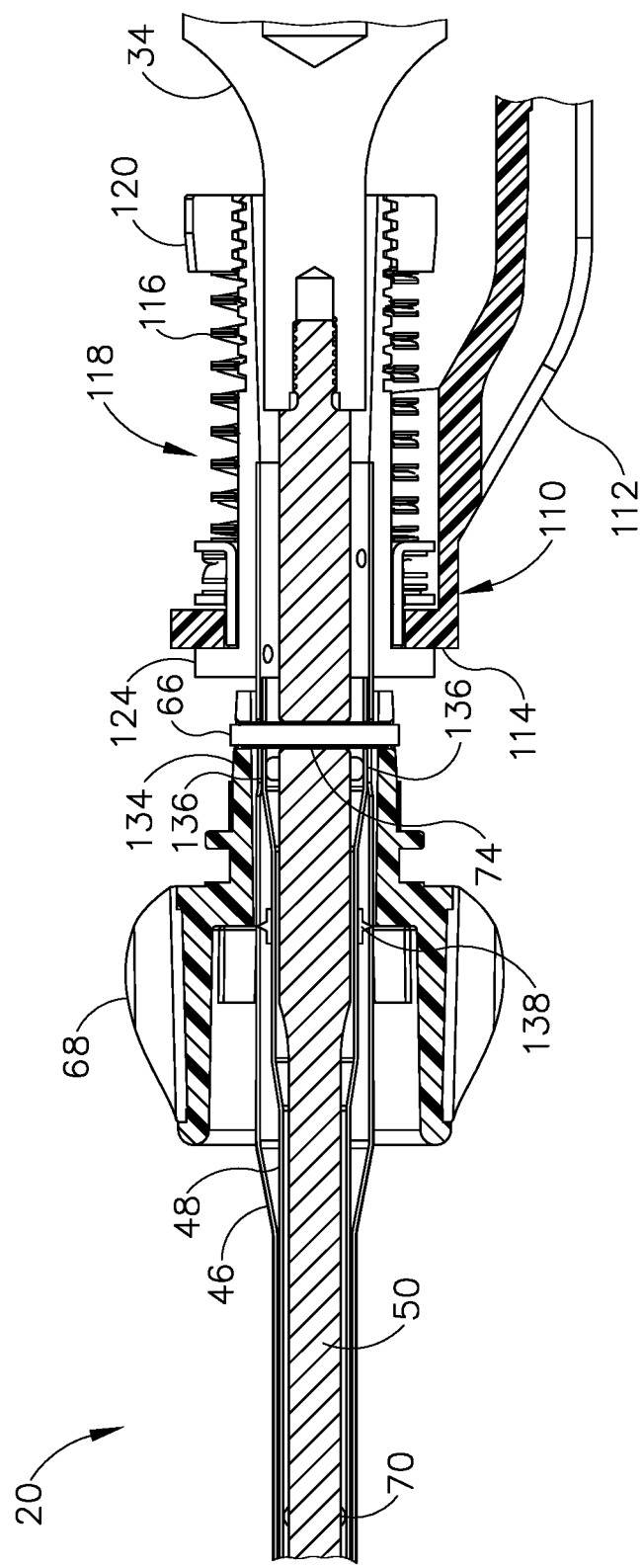
FIG. 8 depicts a partial side sectional view of the surgical instrument of FIG. 1, showing coupling of the shaft assembly, including an ultrasonic waveguide, to the handle assembly.

FIG. 8 shows additional details of shaft assembly (20) and select components of actuation assembly (102) described above, as well as a coupling of a proximal end of ultrasonic waveguide (50) to a distal end of ultrasonic transducer (34). As described above, outer tube (46) is configured to translate longitudinally relative to inner tube (48) and waveguide (50) to move clamp arm (38) between its open and closed positions. In the same configuration, retaining pin (66) extends transversely through a proximal collar (134) of rotation knob (68) and through outer tube, inner tube, and waveguide (50) to thereby secure each of these components rotationally relative to one another, as described above. To accommodate longitudinal translation of outer tube (46) relative to the remaining components of shaft assembly (20), outer tube (46) includes a pair of elongate slots (136) through which retaining pin (66) extends, as shown in FIG. 8. Further, a proximal portion of inner tube (48) may be supported radially within outer tube (46) by a tube support element (138).

In the present example, spring stack (116) is configured to provide a force-limiting feature, such that spring stack (116) resists compression and thereby transfers proximal motion from yoke (114) to outer tube (46) via retaining nut (120) when yoke (114) is driven to actuate outer tube (46) proximally up to a certain force threshold. When clamp arm (38) encounters substantial resistance to further pivotal movement toward ultrasonic blade (36), outer tube (46) will correspondingly provide substantial resistance to further proximal movement, and such resistance will be further provided via retaining nut (120). When this resistance exceeds the predetermined force threshold, and the operator continues to urge trigger (32) toward pistol grip (26), spring stack (116) will begin to compress in response to further proximal motion of yoke (114) while retaining nut (120) and outer tube (46) remain stationary. Spring stack (116) thus absorbs forces that are exerted above the force threshold. Retaining nut (120) may be selectively rotated relative to sleeve (126), via threaded engagement, to compress spring stack (116) against yoke (114) with a desired amount of pre-load. Retaining nut (120) thereby enables adjustability of the predetermined force threshold by allowing adjustment of the pre-load.

C. Exemplary Ultrasonic and Bipolar RF Electrical Circuits

FIGS. 9A and 9B show an exemplary configuration of an ultrasonic electrical circuit (140) and a bipolar RF electrical circuit (142) of surgical instrument (14). As shown in FIG. 9A, generator (12) of surgical system (10) is electrically coupled with and configured to energize each of the electrical circuits (140, 142) to thereby enable surgical instrument (14) to deliver ultrasonic energy and electrosurgical bipolar RF energy to tissue. In various examples, generator (12) may energize ultrasonic electrical circuit (140) and RF electrical circuit (142) simultaneously or in selective, alternating manners. Structural components of ultrasonic electrical circuit (140) and bipolar RF electrical circuit (142) are described below, in respective order, followed by a description of electrical current flow through the circuits (140, 142). As will be described, electrical circuits (140, 142) may share a common electrical return path.

As described above, acoustic assembly (100) of surgical instrument (14) generally includes ultrasonic transducer (34), ultrasonic waveguide (50), and ultrasonic blade (36). As shown in FIG. 9A, ultrasonic transducer (34) of the present example generally includes a first resonator (or "end-bell") (144), a conically shaped second resonator (or "fore-bell") (146), and a transduction portion arranged between end-bell (144) and fore-bell (146) and comprising a plurality of piezoelectric elements (148). A compression bolt (150) extends distally, coaxially through end-bell (144) and piezoelectric elements (148), and is threadedly received within a proximal end of fore-bell (146). A velocity transformer (152) (or "horn") extends distally from fore-bell (146) and couples with a proximal end of ultrasonic waveguide (50), for example via a threaded connection as shown in FIG. 9A. In exemplary versions, ultrasonic transducer (34) may be further configured in accordance with any of the transducer configurations disclosed in the references incorporated by reference herein.

An active transducer electrode (154) is shown arranged between medial and proximal piezoelectric elements (148), and electrically couples with generator (12) via an active transducer lead (156). A return transducer electrode (158) is shown arranged between end-bell (144) and a proximal piezoelectric element (148), and electrically couples with generator (12) via a return transducer lead (160). An active RF lead (162) is electrically coupled with generator (12), and is shown extending from a proximal portion of outer tube (46). It will be understood that the positioning of active RF lead (162) relative to shaft assembly (20) is exemplary only, and that generator (12) may electrically couple with RF electrical circuit (142) at any suitable location along outer tube (46), or alternatively directly at clamp arm (38) so as to bypass outer tube (46), for example. Moreover, in other examples, active RF lead (162) may electrically couple with inner tube (48) instead of outer tube (46), such that RF electrical circuit (142) passes through inner tube (48) instead of outer tube (46).

As shown in FIG. 9A, ultrasonic electrical circuit (140) includes an active electrical path that passes distally through active transducer lead (156) to active transducer electrode (154) and into piezoelectric elements (148). Ultrasonic electrical circuit (140) further includes a return electrical path that passes proximally from piezoelectric elements (148), through return transducer electrode (158) to return transducer lead (160). Generator (12) directs electrical current through the active electrical path to the return electrical path to thereby energize ultrasonic transducer (34) to produce ultrasonic mechanical vibrations, which are communicated via ultrasonic waveguide (50) to ultrasonic blade (36).

As shown in FIGS. 9A and 9B, RF electrical circuit (142) includes an active RF path that passes from active RF lead (162) to outer tube (46), and distally through outer tube (46) to clamp arm (38) via clevis fingers (58). In the present example, flow of RF electrical energy through the RF active path is enabled by electrical coupling of outer tube (46) with clamp arm (38), for example by metal-to-metal contact. The active RF energy flows from clevis arms (52) into clamp arm electrode (42), and then into tissue (164). As described in greater detail below, clamp arm electrode (42) may be in the form of a clamping-side surface of clamp arm (38), formed integrally with and thereby electrically coupled with the remainder of clamp arm (38). In various examples, the entirety of clamp arm (38), including or not including clamp pad (40), may be formed of an electrically conductive material, such as a metal, such that the entire clamp arm (38) serves as the clamp arm electrode (42).

RF electrical circuit (142) further includes a return electrical path that directs RF energy proximally from end effector (22) to handle assembly (18), via ultrasonic waveguide (50). As shown in FIG. 9B, when tissue (164) is electrically coupled with clamp arm electrode (42) and blade electrode (44) simultaneously, for example by direct or indirect contact, RF energy passes from the active RF path, through tissue (164), to the return RF path, via blade electrode (44). From blade electrode (44), the RF energy returns proximally through waveguide (50) and passes into ultrasonic transducer (34), as described further below. In this manner, tissue (164) is treated with bipolar RF energy provided by generator (12).

In exemplary configurations, blade electrode (44) may be defined by a selected clamping-side surface of ultrasonic blade (36). In other configurations, the entirety of ultrasonic blade (36) may serve as blade electrode (44). In various such configurations, blade electrode (44) is electrically coupled with ultrasonic blade (36), which is electrically coupled with ultrasonic waveguide (50), which in turn is electrically coupled with ultrasonic transducer (34). Accordingly, within the RF return path, RF energy passes proximally from blade electrode (44), through ultrasonic blade (36) to ultrasonic waveguide (50), and ultimately to ultrasonic transducer (34). As shown in FIG. 9A, upon entering ultrasonic transducer (34), the return RF energy passes proximally through fore-bell (146) and compression bolt (150), and from compression bolt (150) through end-bell (144) to return transducer electrode (158), and to return transducer lead (160). Accordingly, RF electrical circuit (142) and ultrasonic electrical circuit (140) share a common electrical return path through return transducer electrode (158) and return transducer lead (160).

While the exemplary configuration described above employs clamp arm electrode (42) as an active electrode and blade electrode (44) as a return electrode, it will be appreciated that a reverse designation may be employed, in which blade electrode (44) is an active electrode and clamp arm electrode (42) is a return electrode. In such a configuration, the ultrasonic electrical circuit (140) and RF electrical circuit (142) would share a common active electrical path through transducer lead (160) and transducer electrode (158) back to generator (12). Furthermore, in alternative arrangements, RF electrical circuit (142) may pass through inner tube (48) rather than outer tube (46), or RF electrical circuit (142) may bypass inner and outer tubes (46, 48) all together.

As described above, generator (12) may be configured to energize ultrasonic electrical circuit (140) and RF electrical circuit (142) simultaneously, to enable surgical instrument (14) to treat tissue with simultaneous application of ultrasonic energy and electrosurgical bipolar RF energy. Additionally, or alternatively, generator (12) may be configured to energize ultrasonic electrical circuit (140) and RF electrical circuit (142) in alternating manners, to allow for selective application of only one of ultrasonic energy or bipolar RF energy to tissue at a given time. For instance, generator (12) may energize only RF electrical circuit (142) for sealing tissue with bipolar RF energy, leaving ultrasonic blade (36) inactive. Alternatively, generator (12) may energize only ultrasonic electrical circuit (140) for cutting and/or sealing tissue with ultrasonic energy, leaving RF electrodes (42, 44) inactive.

Surgical instrument (14) may include various features for inhibiting undesired electrical shorting of the RF active path and the RF return path of RF electrical circuit (142), for example at locations proximal of clamp arm electrode (42) and blade electrode (44). For instance, retaining pin (66) shown in FIG. 9A may be encased in an electrically insulative sheath (166) that prevents shorting between outer tube (46) and ultrasonic waveguide (50). Similarly, clamp arm pivot pin (56) shown in FIG. 9B may be encased in an electrically insulative sheath that prevents transfer of electrical energy from clamp arm (38) to inner tube (48), which encases ultrasonic waveguide (50). Further, as described in greater detail below with reference to FIGS. 10-17, select portions of ultrasonic blade (36), ultrasonic waveguide (50), outer tube (46), and/or inner tube (48) may be coated with a layer of electrically insulative material configured to prevent shorting of RF electrical circuit (142).

D. Exemplary Electrically Insulative Material Layers

As described above, surgical instrument (14) may include various features that inhibit undesired electrical shorting of the active and return paths of RF electrical circuit (142). For example, as described below with reference to FIGS. 10-17, various select portions of ultrasonic blade (36), clamp arm (38), ultrasonic waveguide (50), outer tube (46), and/or inner tube (48) may be coated with an electrically insulative material to prevent such shorting. In exemplary variations, any of the electrically insulative material layers described below may also be thermally insulative. By way of example only, the insulative material layers described below may comprise a Parylene coating.

Figure 10:
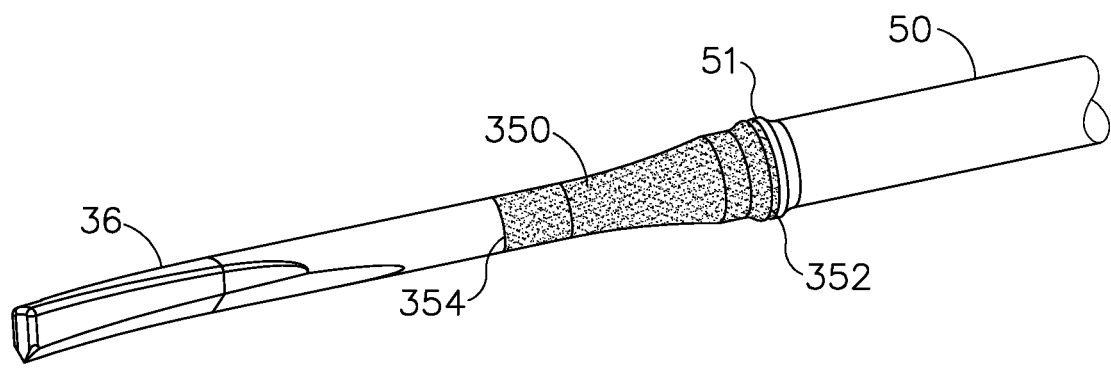
FIG. 10 depicts a perspective view of the ultrasonic blade of the surgical instrument of FIG. 1, having an electrically insulative material applied to an outer surface thereof.
Figure 11:
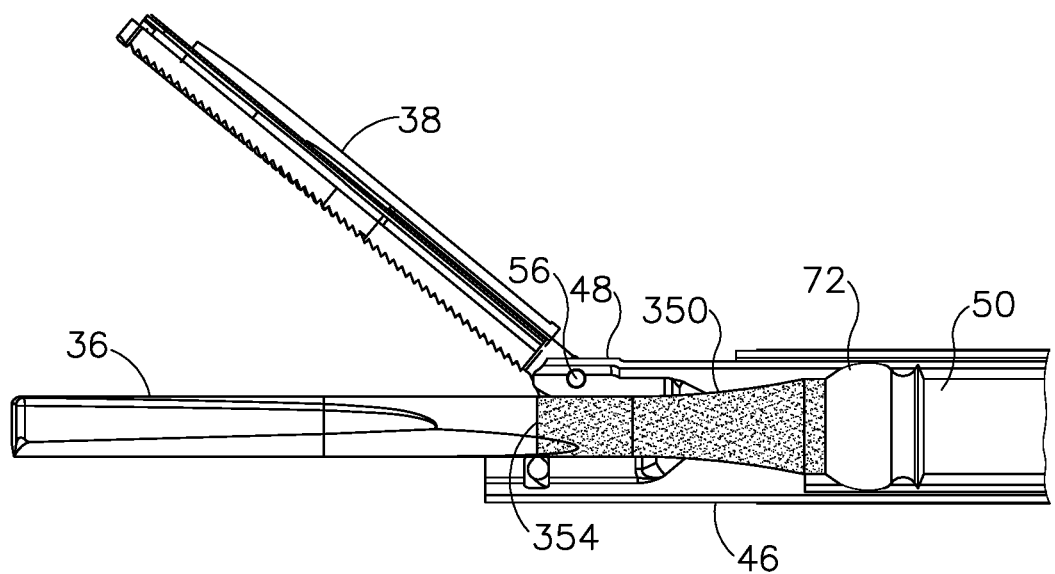
FIG. 11 depicts a sectional side view of the end effector of the surgical instrument of FIG. 1, incorporating the treated ultrasonic blade of FIG. 10.

FIGS. 10 and 11 show an exemplary electrically insulative material layer (350) applied to an outer surface of ultrasonic blade (36). Insulative material layer (350) extends distally from a proximal end (352) that encapsulates at least a portion of distal nodal flange (51) of waveguide (50), to a distal end (354) located distally of clamp arm pivot pin (56). Insulative material layer (350) may extend fully circumferentially about the covered portion of ultrasonic blade (36). As shown in FIG. 11, overmold member (72) overlaps the proximal end (352) of insulative material layer (350).

Figure 12:
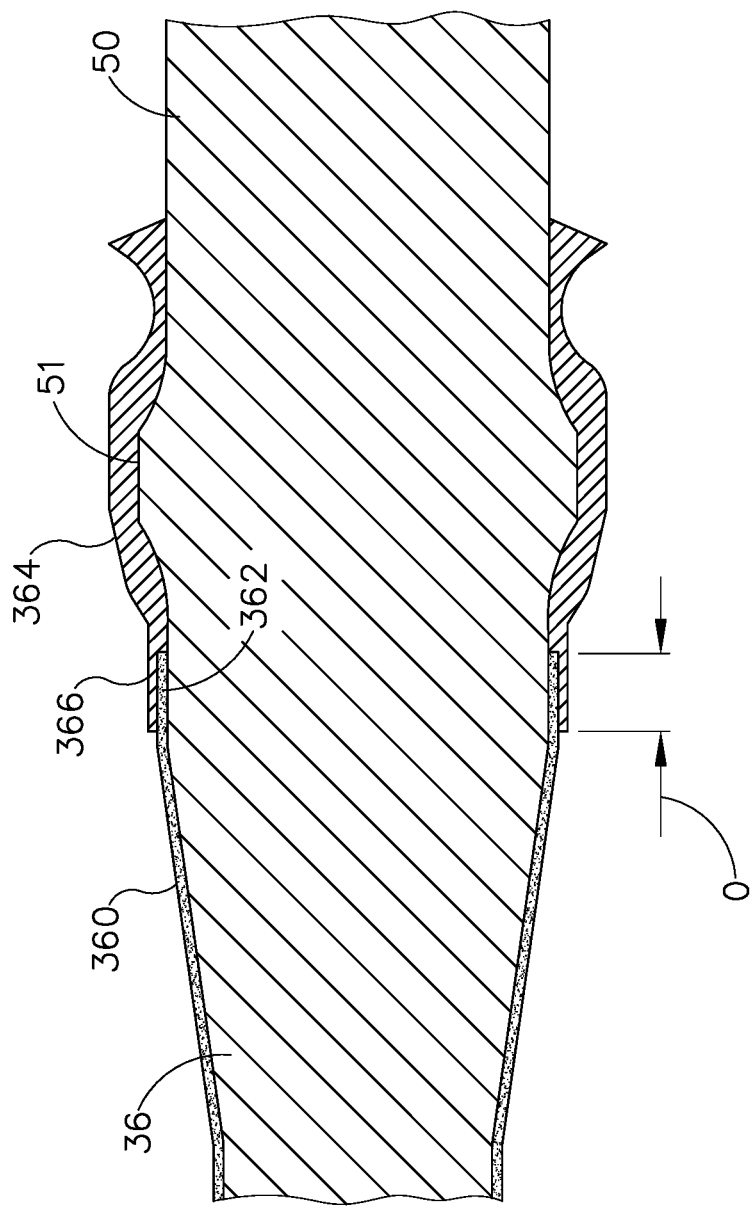
FIG. 12 depicts a sectional side view of an exemplary nodal support element mounted to the ultrasonic blade of FIG. 10, showing overlap of the nodal support element with the electrically insulative material on the ultrasonic blade.

FIG. 12 shows another exemplary electrically insulative material layer (360) applied to the outer surface of ultrasonic blade (36). Insulative material layer (360) is substantially identical to insulative material layer (350) described above, except that insulative layer (360) includes a proximal end (362) disposed just distally of distal nodal flange (51) of waveguide (50). Further, waveguide (50) is shown fitted with an overmold member (364) that is substantially identical to overmold member (72) described above, except that overmold member (364) includes a distally extending, thin-walled annular flap (366) that overlaps proximal end (362) of insulative material layer (360) by an axial overlap distance (O). The portion of overmold member (364) located proximally of insulative material layer (360) is able to adhere to the outer surface of waveguide (50) and ultrasonic blade (36), while the portion of annular flap (366) that overlaps insulative material layer (360) does not adhere to the outer surface.

Annular flap (366) is provided with an axial length suitable to ensure overlap of at least a portion of flap (366) and proximal end (362) of insulative material layer (360) for various axial lengths of proximal end (362) falling within a known tolerance range experienced during an insulative layer application process. This configuration ensures effective insulative covering of a portion of ultrasonic blade (36) extending distally from nodal flange (51) to a location just distal of clamp arm pivot pin (56).

FIGS. 13 and 14 show another exemplary electrically insulative material layer (370), applied to outer and inner surfaces of inner tube (48) of surgical instrument (14). Insulative layer (370) extends proximally from distal end (54) of inner tube (48) to any suitable location along each of the inner and outer surfaces of inner tube (48). In the exemplary configuration shown, insulative layer (370) is limited to distal portions of the inner and outer surfaces of inner tube (48).

Figure 15:
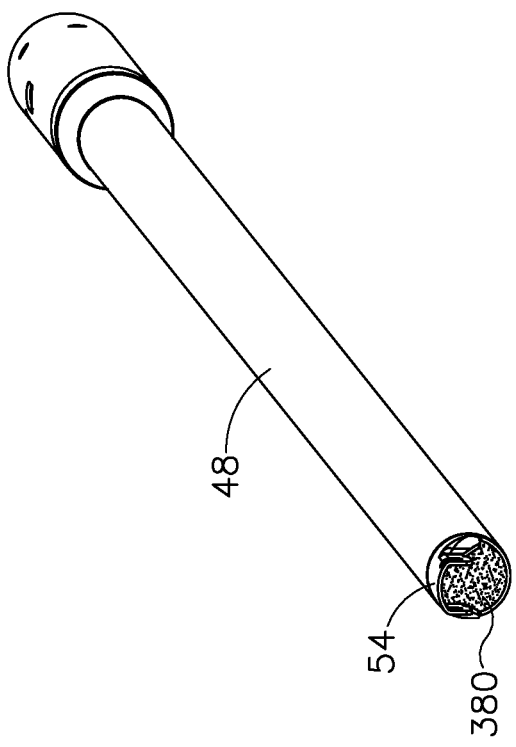
FIG. 15 depicts a perspective view of the inner tube of the ultrasonic instrument of FIG. 1, having an electrically insulative material applied to inner surfaces thereof.
Figure 16:
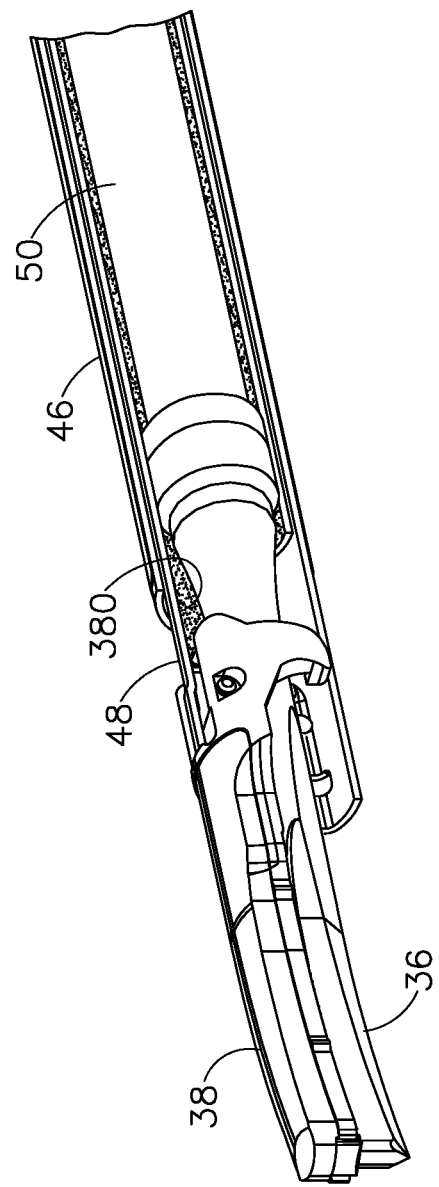
FIG. 16 depicts a sectional perspective view of the end effector and shaft assembly of the surgical instrument of FIG. 1, incorporating the treated inner tube of FIG. 15.

FIGS. 15 and 16 show another exemplary electrically insulative material layer (380), applied to only an inner surface of inner tube (48). Insulative layer (380) extends proximally from distal end (54) of inner tube (48) to any suitable location along the inner surface of inner tube (48).

FIG. 17 shows another exemplary electrically insulative material layer (390), applied to the outer surface of the non-clamping side of clamp arm (38). Insulative layer (390) extends proximally from a distal tip of clamp arm (38) to distal ends of clevis arms (52), leaving clevis arms (52) uncovered so as to remain electrically coupled with clamp arm electrode (42). Since the entire body clamp arm (38) is formed of an electrically conductive material in this example, and since the entire body of clamp arm (38) is electrically energized when end effector (22) delivers bipolar RF energy to tissue, the presence of insulative layer (390) on the non-clamping side of clamp arm (38) effectively limits clamp arm electrode (42) to being presented in the form of the clamping side of clamp arm (38), and thereby enhances the efficiency of bipolar RF energy delivered by clamp surgical instrument (14).

It will be appreciated that in alternative configurations not shown herein, any suitable portion of shaft assembly (20) and/or end effector (22), including ultrasonic blade (36), clamp arm (38), outer tube (46), inner tube (48), and/or ultrasonic waveguide (50), may be coated with an electrically insulative material layer to prevent electrical shorting of RF electrical circuit (142).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft; (b) an ultrasonic transducer; (c) a waveguide acoustically coupled with the ultrasonic transducer and extending distally through the shaft; (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, (iii) a first RF electrode provided by the clamp arm, wherein the first RF electrode is electrically coupled with a first RF electrical path of the surgical instrument, and (iv) a second RF electrode provided by the ultrasonic blade, wherein the second RF electrode is electrically coupled with a second RF electrical path of the surgical instrument, wherein the first and second RF electrodes are operable to seal tissue with bipolar RF energy; and (e) an electrically insulative layer configured to prevent shorting between the first RF electrical path and the second RF electrical path, wherein the electrically insulative layer is provided on at least a portion of at least one of the ultrasonic blade, the waveguide, the shaft, or the clamp arm.

Example 2

The surgical instrument of Example 1, wherein the first RF electrode comprises an active electrode and the first RF electrical path comprises an active path, wherein the Example 3

The surgical instrument of any of the previous Examples, wherein the electrically insulative layer is provided on a portion of the ultrasonic blade.

Example 4

The surgical instrument of Example 3, wherein the electrically insulative layer extends fully circumferentially about the portion of the ultrasonic blade.

Example 5

The surgical instrument of any of the previous Examples, wherein the clamp arm is pivotably coupled to the shaft with a pivot pin, wherein the electrically insulative layer extends longitudinally along the ultrasonic blade between a proximal end arranged proximally of the pivot pin and a distal end arranged distally of the pivot pin.

Example 6

The surgical instrument of any of the previous Examples, wherein the ultrasonic blade extends distally from a distal-most acoustic node of the waveguide, wherein the electrically insulative layer encapsulates at least a portion of the distal-most acoustic node.

Example 7

The surgical instrument of any of the previous Examples, further comprising an annular overmold member that encircles the waveguide at a distal-most acoustic node thereof, wherein a distal portion of the annular overmold member overlaps a portion of the electrically insulative layer.

Example 8

The surgical instrument of any of the previous Examples, wherein the shaft comprises an outer tube and an inner tube, wherein the waveguide extends through the inner tube, wherein one of the outer tube or the inner tube comprises a translating tube operable to translate relative to the other of the outer tube or the inner tube to actuate the clamp arm relative to the ultrasonic blade, wherein the first RF electrode is electrically coupled with the translating tube such that the first RF electrical path passes through the translating tube, wherein the second RF electrical path passes through the ultrasonic blade and the waveguide.

Example 9

The surgical instrument of any of the previous Examples, wherein the electrically insulative layer is provided on the inner tube, wherein the electrically insulative layer is configured to prevent electrical shorting between the translating tube and the waveguide.

Example 10

The surgical instrument of Example 9, wherein the electrically insulative layer is provided on an inner surface of the inner tube.

Example 11

The surgical instrument of any of the previous Examples, wherein the electrically insulative layer is provided on a portion of the clamp arm.

Example 12

The surgical instrument of Example 11, wherein the clamp arm includes a clamping side and a non-clamping side, wherein the clamping side is configured to clamp tissue against the ultrasonic blade, wherein the electrically insulative layer is provided on the non-clamping side.

Example 13

The surgical instrument of any of the previous Examples, wherein the electrically insulative layer is also thermally insulative.

Example 14

The surgical instrument of any of the previous Examples, wherein the electrically insulative layer comprises a coating.

Example 15

The surgical instrument of any of the previous Examples, wherein the electrically insulative layer comprises Parylene.

Example 16

A surgical instrument comprising: (a) a shaft; (b) an ultrasonic transducer; (c) a waveguide acoustically coupled with the ultrasonic transducer and extending distally through the shaft; (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, (iii) a first RF electrode provided by the clamp arm, wherein the first RF electrode is electrically coupled with a first RF electrical path of the surgical instrument, and (iv) a second RF electrode provided by the ultrasonic blade, wherein the second RF electrode is electrically coupled with a second RF electrical path of the surgical instrument, wherein the first and second RF electrodes are operable to seal tissue with bipolar RF energy; and (e) an electrically insulative layer configured to prevent shorting between the first RF electrical path and the second RF electrical path, wherein the electrically insulative layer is provided on at least a portion of the ultrasonic blade.

Example 17

The surgical instrument of Example 16, wherein the clamp arm is pivotably coupled to the shaft with a pivot pin, wherein the electrically insulative layer extends longitudinally along the ultrasonic blade between a proximal end arranged proximally of the pivot pin and a distal end arranged distally of the pivot pin.

Example 18

The surgical instrument of any of Examples 16 through 17, wherein the electrically insulative layer is also provided on a portion of the shaft.

Example 19

A surgical instrument comprising: (a) a shaft; (b) an ultrasonic transducer; (c) a waveguide acoustically coupled with the ultrasonic transducer and extending distally through the shaft; (d) an end effector arranged at a distal end of the shaft, wherein the end effector comprises: (i) an ultrasonic blade acoustically coupled with the waveguide, wherein the ultrasonic transducer is operable to drive the waveguide and the ultrasonic blade with ultrasonic energy, (ii) a clamp arm movable relative to the ultrasonic blade for clamping tissue therebetween, (iii) a first RF electrode provided by the clamp arm, wherein the first RF electrode is electrically coupled with a first RF electrical path of the surgical instrument, and (iv) a second RF electrode provided by the ultrasonic blade, wherein the second RF electrode is electrically coupled with a second RF electrical path of the surgical instrument, wherein the first and second RF electrodes are operable to seal tissue with bipolar RF energy; and (e) an electrically insulative layer configured to prevent shorting between the first RF electrical path and the second RF electrical path, wherein the electrically insulative layer is provided on at least a portion of the shaft.

Example 20

The surgical instrument of Example 19, wherein the shaft comprises an outer tube and an inner tube, wherein the waveguide extends through the inner tube, wherein one of the outer tube or the inner tube comprises a translating tube operable to translate relative to the other of the outer tube or the inner tube to actuate the clamp arm relative to the ultrasonic blade, wherein the first RF electrode is electrically coupled with the translating tube such that the first RF electrical path passes through the translating tube, wherein the second RF electrical path passes through the ultrasonic blade and the waveguide, wherein the electrically insulative layer is provided on at least a portion of the inner tube and is configured to prevent electrical shorting between the translating tube and the waveguide.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pat. App. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. Pat. App. No. 15/967,746, entitled "Combination Ultrasonic and Electrosurgical Instrument Having Slip Ring Electrical Contact Assembly," filed on May 1, 2018, published as U.S. Pub. No. 2018/0333185 on Nov. 22, 2018; U.S. Pat. App. No. 15/967,751, entitled "Combination Ultrasonic and Electrosurgical Instrument Having Curved Ultrasonic Blade," filed on May 1, 2018, published as U.S. Pub. No. 2018/0333180 on Nov. 22, 2018; U.S. Pat. App. No. 15/967,753, entitled "Combination Ultrasonic and Electrosurgical Instrument Having Clamp Arm Electrode," filed on May 1, 2018, published as U.S. Pub. No. 2018/0333183 on Nov. 22, 2018; U.S. Pat. App. No. 15/967,759, entitled "Combination Ultrasonic and Electrosurgical Instrument Having Ultrasonic Waveguide With Distal Overmold Member," filed on May 1, 2018, published as U.S. Pub. No. 2018/0333183 on Nov. 22, 2018; U.S. Pat. App. No. 15/967,761, entitled "Combination Ultrasonic and Electrosurgical System Having Generator Filter Circuitry," filed on May 1, 2018, published as U.S. Pub. No. 2018/0333184 on Nov. 22, 2018; and/or U.S. Pat. App. No. 15/967,764, entitled "Combination Ultrasonic and Electrosurgical System Having EEPROM and ASIC Components," filed on May 1, 2018, published as U.S. Pub. No. 2018/0333186 on Nov. 22, 2018. The disclosure of each of these applications is incorporated by reference herein.

Further, any one or more of the teachings, expressions, embodiments, examples, etc. described herin may be combined with any one or more of the teachings, expressions, embodiments, examples, etc. described in U.S. Pat. App. No. 15/967,758, entitled "Combination Ultrasonic and Electrosurgical Instrument with Clamp Arm Position Input and Method for Identifying Tissue State," filed on May 1, 2018, published U.S. Pub. No. 2018/0333182 on Nov. 22, 2018, U.S. Pat. App. No. 15/967,763, entitled "Combination Ultrasonic and Electrosurgical Instrument with Adjustable Energy Modalities and Method for Sealing Tissue and Inhibiting TIssue Resection," filed on May 1, 2018, published as U.S. Pub. No. 2018/0333185 on Nov. 22, 2018; U.S. Pat. App. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 2018; U.S. Pat. App. No. 15/967,775, entitled "Combination Ultrasonic and Electrosurgical Instrumenmt with Adjustable Energy Modalities and Method for Limiting Blade Temperature," filed on May 1, 2018, published as U.S. Pub. No. 2018/0333188 on Nov. 22, 2018; U.S. Pat. App. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 Nov. 22, 2018; and/or U.S. Pat. App. No. 15/967,784, entitled "Combination Ultrasonic and Electrosurgical Instrument and Method for Sealing Tissue in Successive Phases," filed on May 1, 2018, published as U.S. Pub. No. 2018/0333190 on Nov. 22, 2018. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a shaft;
   (b) an ultrasonic transducer;
   (c) a waveguide acoustically coupled with the ultrasonic transducer and extending distally through the shaft;
   (d) an end effector arranged at a distal end of the shaft, wherein the end effector comprises:
      (i) an ultrasonic blade acoustically coupled with the waveguide, wherein the ultrasonic transducer is operable to drive the waveguide and the ultrasonic blade with ultrasonic energy,
      (ii) a clamp arm movable relative to the ultrasonic blade for clamping tissue therebetween,
      (iii) a first RF electrode provided by the clamp arm, wherein the first RF electrode is electrically coupled with a first RF electrical path of the surgical instrument, and
      (iv) a second RF electrode provided by the ultrasonic blade, wherein the second RF electrode is electrically coupled with a second RF electrical path of the surgical instrument,
   wherein the first and second RF electrodes are operable to seal tissue with bipolar RF energy; and
   (e) an electrically insulative layer configured to prevent shorting between the first RF electrical path and the second RF electrical path, wherein the electrically insulative layer is provided on at least a portion of the waveguide,
   wherein the ultrasonic blade extends distally from a distal-most acoustic node of the waveguide, wherein the electrically insulative layer encapsulates at least a portion of the distal-most acoustic node.

2. The surgical instrument of claim 1, wherein the first RF electrode comprises an active electrode and the first RF electrical path comprises an active path, wherein the second RF electrode comprises a return electrode and the second RF electrical path comprises a return path.

3. The surgical instrument of claim 1, wherein the electrically insulative layer is further provided on a portion of the ultrasonic blade.

4. The surgical instrument of claim 3, wherein the electrically insulative layer extends fully circumferentially about the portion of the ultrasonic blade.

5. The surgical instrument of claim 3, wherein the clamp arm is pivotably coupled to the shaft with a pivot pin, wherein the electrically insulative layer extends longitudinally along the ultrasonic blade between a proximal end arranged proximally of the pivot pin and a distal end arranged distally of the pivot pin.

6. The surgical instrument of claim 1, further comprising an annular overmold member that encircles the waveguide at the distal-most acoustic node thereof, wherein a distal portion of the annular overmold member overlaps a portion of the electrically insulative layer.

7. The surgical instrument of claim 1, wherein the shaft comprises an outer tube and an inner tube, wherein the waveguide extends through the inner tube, wherein one of the outer tube or the inner tube comprises a translating tube operable to translate relative to the other of the outer tube or the inner tube to actuate the clamp arm relative to the ultrasonic blade, wherein the first RF electrode is electrically coupled with the translating tube such that the first RF electrical path passes through the translating tube, wherein the second RF electrical path passes through the ultrasonic blade and the waveguide.

8. The surgical instrument of claim 7, further comprising a second electrically insulative layer provided on the inner tube, wherein the second electrically insulative layer is configured to prevent electrical shorting between the translating tube and the waveguide.

9. The surgical instrument of claim 8, wherein the second electrically insulative layer is provided on an inner surface of the inner tube.

10. The surgical instrument of claim 1, further comprising a second electrically insulative layer provided on a portion of the clamp arm.

11. The surgical instrument of claim 10, wherein the clamp arm includes a clamping side and a non-clamping side, wherein the clamping side is configured to clamp tissue against the ultrasonic blade, wherein the second electrically insulative layer is provided on the non-clamping side.

12. The surgical instrument of claim 1, wherein the electrically insulative layer is also thermally insulative.

13. The surgical instrument of claim 1, wherein the electrically insulative layer comprises a coating.

14. The surgical instrument of claim 1, wherein the electrically insulative layer comprises Parylene.

15. A surgical instrument comprising:
   (a) a shaft;
   (b) an ultrasonic transducer;
   (c) a waveguide acoustically coupled with the ultrasonic transducer and extending distally through the shaft;
   (d) an end effector arranged at a distal end of the shaft, wherein the end effector comprises:
      (i) an ultrasonic blade acoustically coupled with the waveguide, wherein the ultrasonic transducer is operable to drive the waveguide and the ultrasonic blade with ultrasonic energy,
      (ii) a clamp arm movable relative to the ultrasonic blade for clamping tissue therebetween,
      (iii) a first RF electrode provided by the clamp arm, wherein the first RF electrode is electrically coupled with a first RF electrical path of the surgical instrument, and
      (iv) a second RF electrode provided by the ultrasonic blade, wherein the second RF electrode is electrically coupled with a second RF electrical path of the surgical instrument,
   wherein the first and second RF electrodes are operable to seal tissue with bipolar RF energy; and
   (e) an electrically insulative layer configured to prevent shorting between the first RF electrical path and the second RF electrical path, wherein the electrically insulative layer is provided on at least a portion of the ultrasonic blade,
   wherein the ultrasonic blade extends distally from a distal-most acoustic node of the waveguide, wherein the electrically insulative layer encapsulates at least a portion of the distal-most acoustic node.

16. The surgical instrument of claim 15, wherein the clamp arm is pivotably coupled to the shaft with a pivot pin, wherein the electrically insulative layer extends longitudinally along the ultrasonic blade between a proximal end arranged proximally of the pivot pin and a distal end arranged distally of the pivot pin.

17. The surgical instrument of claim 16, wherein the distal end of the electrically insulative layer is arranged proximally of a distal end of the ultrasonic blade.

18. The surgical instrument of claim 15, wherein the electrically insulative layer is also provided on a portion of the shaft.

19. A surgical instrument comprising:
(a) a shaft;
(b) an ultrasonic transducer;
(c) a waveguide acoustically coupled with the ultrasonic transducer and extending distally through the shaft;
(d) an end effector arranged at a distal end of the shaft, wherein the end effector comprises:
  (i) an ultrasonic blade acoustically coupled with the waveguide, wherein the ultrasonic transducer is operable to drive the waveguide and the ultrasonic blade with ultrasonic energy,
  (ii) a clamp arm movable relative to the ultrasonic blade for clamping tissue therebetween,
  (iii) a first RF electrode provided by the clamp arm, wherein the first RF electrode is electrically coupled with a first RF electrical path of the surgical instrument, and
  (iv) a second RF electrode provided by the ultrasonic blade, wherein the second RF electrode is electrically coupled with a second RF electrical path of the surgical instrument,
  wherein the first and second RF electrodes are operable to seal tissue with bipolar RF energy; and
(e) an electrically insulative layer configured to prevent shorting between the first RF electrical path and the second RF electrical path, wherein the electrically insulative layer is provided on at least a portion of the clamp arm,
wherein the clamp arm includes a clamping side and a non-clamping side, wherein the clamping side is configured to clamp tissue against the ultrasonic blade, wherein the electrically insulative layer is provided on the non-clamping side, wherein the non-clamping side of the clamp arm includes an outer surface facing away from the ultrasonic blade, wherein the electrically insulative layer is provided on the outer surface of the non-clamping side.

20. The surgical instrument of claim 19, wherein the electrically insulative layer is configured to contact tissue faced by the outer surface of the non-clamping side.

* * * * *